(12) United States Patent
Kim et al.

(10) Patent No.: US 10,662,169 B2
(45) Date of Patent: May 26, 2020

(54) CATECHOL DERIVATIVE AND PHARMACEUTICAL COMPOSITION COMPRISING THE SAME

(71) Applicant: AUTOPHAGYSCIENCES INC., Seoul (KR)

(72) Inventors: Hwan Mook Kim, Daejeon (KR); Kwang Won Jeong, Incheon (KR); Seung Hyun Oh, Goyang-si (KR); Sun Ki Kim, Seoul (KR); Jung Ju Kim, Seoul (KR); Seong-Won Song, Gunpo-si (KR)

(73) Assignee: AUTOPHAGYSCIENCES INC., Seoul (KR)

( * ) Notice: Subject to any disclaimer, the term of this patent is extended or adjusted under 35 U.S.C. 154(b) by 0 days.

(21) Appl. No.: 15/751,707

(22) PCT Filed: Aug. 19, 2016

(86) PCT No.: PCT/KR2016/009196
§ 371 (c)(1),
(2) Date: Feb. 9, 2018

(87) PCT Pub. No.: WO2017/034242
PCT Pub. Date: Mar. 2, 2017

(65) Prior Publication Data
US 2018/0244644 A1 Aug. 30, 2018

(30) Foreign Application Priority Data

Aug. 21, 2015 (KR) .................. 10-2015-0118247

(51) Int. Cl.
| | |
|---|---|
| *C07D 333/38* | (2006.01) |
| *C07D 409/04* | (2006.01) |
| *C07D 409/14* | (2006.01) |
| *A61K 31/381* | (2006.01) |
| *C07D 401/14* | (2006.01) |
| *A61K 31/426* | (2006.01) |
| *C07D 333/10* | (2006.01) |
| *C07D 277/20* | (2006.01) |
| *A61P 1/16* | (2006.01) |
| *C07D 417/04* | (2006.01) |

(52) U.S. Cl.
CPC .......... *C07D 333/38* (2013.01); *A61K 31/381* (2013.01); *A61K 31/426* (2013.01); *A61P 1/16* (2018.01); *C07D 277/20* (2013.01); *C07D 333/10* (2013.01); *C07D 401/14* (2013.01); *C07D 409/04* (2013.01); *C07D 409/14* (2013.01); *C07D 417/04* (2013.01)

(58) Field of Classification Search
CPC .. C07D 333/38; C07D 409/04; C07D 409/14; C07D 417/04; A61P 1/16
USPC .................................................... 548/281.4
See application file for complete search history.

(56) References Cited

U.S. PATENT DOCUMENTS

| | | | | |
|---|---|---|---|---|
| 4,946,855 A | * | 8/1990 | Yoshinaga | ........... C07D 417/12 514/314 |
| 2012/0165370 A1 | | 6/2012 | Tang et al. | |
| 2013/0251654 A1 | | 9/2013 | Kwon et al. | |

FOREIGN PATENT DOCUMENTS

| | | |
|---|---|---|
| WO | WO 2005/030206 A1 | 4/2005 |
| WO | WO 2005/079791 A1 | 9/2005 |
| WO | WO 2007/035478 A2 | 3/2007 |
| WO | WO 2009/024095 A1 | 2/2009 |

OTHER PUBLICATIONS

Synthesis and biological activity of 5-arylthiophene-2-carboxylic acid derivatives. Shvedov et al. (Year: 1979).*
Andrew Thrburn, Autophagy and diseases. (Year: 2018).*
Schoffmann, A. et al. "Efficient modulation of γ-aminobutyric acid type A receptors by piperine derivatives", Journal of Medicinal Chemistry, vol. 57, No. 13, pp. 5602-5619, 2014.
Chemical Abstract compound, STN express. RN 921180-99-6 Registry (Entered STN: Feb. 15, 2007).
Chemical Abstract compound, STN express. RN 1386641-70-8 Registry (Entered STN: Aug. 6, 2012).
Chemical Abstract compound, STN express. RN 924399-41-7 Registry (Entered STN: Mar. 2, 2007).
Chemical Abstract compound, STN express. RN 1387633-13-7 Registry (Entered STN: Aug. 7, 2012).
Chemical Abstract compound, STN express. RN 1355555-80-4 Registry (Entered STN: Feb. 7, 2012).
International Search Report of PCT Application No. PCT/KR2016/009196, dated Feb. 21, 2017.
Wang, W. L. et al. "Discovery of Inhibitors of *Escherichia coli* Methionine Aminopeptidase with the Fe(II)-Form Selectivity and Antibacterial Activity". *Journal of Medicinal Chemistry*, 2008, vol. 51, No. 19, pp. 6110-6120.
Farrell, G. C. et al., "Nonalcoholic fatty liver disease: From steatosis to cirrhosis". 2006. Hepatology, vol. 43, pp. S99-S112. doi:10.1002/hep.20973.
Klionsky, D. J. et al., "Autophagy as a Regulated Pathway of Cellular Degradation." *Science*, vol. 290, No. 5497, 2000, pp. 1717-1721.
Levine, Beth et al., "Development by Self-Digestion: Molecular Mechanisms and Biological Functions of Autophagy". 2004. *Developmental Cell*, vol. 6, No. 4, pp. 463-477.
Codogno, Patrice et al., "Autophagy in the Liver." *Journal of Hepatology*, vol. 59, No. 2, 2013, pp. 389-391.
Rautou, Pierre-Emmanuel, et al., "Autophagy in Liver Diseases." *Journal of Hepatology*, vol. 53, No. 6, 2010, pp. 1123-1134.

(Continued)

*Primary Examiner* — Rita J Desai
(74) *Attorney, Agent, or Firm* — Pearl Cohen Zedek Latzer Baratz LLP (57) ABSTRACT

The present invention relates to a compound represented by Chemical Formula 1 or a pharmaceutically acceptable salt thereof. The compound according to the present invention can be usefully used for the prevention or treatment of autophagy-related diseases.

13 Claims, 6 Drawing Sheets

(56) References Cited

OTHER PUBLICATIONS

Czaja, Mark J., et al., "Functions of Autophagy in Normal and Diseased Liver." *Autophagy*, vol. 9, No. 8, 2013, pp. 1131-1158.
Hay, N. et al., "Upstream and Downstream of MTOR." *Genes & Development*, vol. 18, No. 16, 2004, pp. 1926-1945.
Yang, Qian, et al., "Expanding MTOR Signaling." *Cell Research*, vol. 17, No. 8, 2007, pp. 666-681.
Schmelzle, Tobias, et al., "TOR, a Central Controller of Cell Growth." *Cell*, vol. 103, No. 2, 2000, pp. 253-262.
Sarbassov, Dos D, et al., "Growing Roles for the MTOR Pathway." *Current Opinion in Cell Biology*, vol. 17, No. 6, 2005, pp. 596-603.
Reif, Shimon, et al., "The Role of Focal Adhesion Kinase-Phosphatidylinositol 3-Kinase-Akt Signaling in Hepatic Stellate Cell Proliferation and Type I Collagen Expression." *Journal of Biological Chemistry*, vol. 278, No. 10, 2002, pp. 8083-8090.
Gäbele, Erwin, et al., "The Role of p70S6Kin Hepatic Stellate Cell Collagen Gene Expression and Cell Proliferation." *Journal of Biological Chemistry*, vol. 280, No. 14, 2005, pp. 13374-13382.
Gäbele, Erwin, et al., "Liver Fibrosis: Signals Leading to the Amplification of the Fibrogenic Hepatic Stellate Cell." *Frontiers in Bioscience*, vol. 8, No. 4, 2003, pp. d69-d77.
Biecker, E. et al., "Long-Term Treatment of Bile Duct-Ligated Rats with Rapamycin (Sirolimus) Significantly Attenuates Liver Fibrosis: Analysis of the Underlying Mechanisms." *Journal of Pharmacology and Experimental Therapeutics*, vol. 313, No. 3, 2005, pp. 952-961.
Neef, Markus, et al., "Low-Dose Oral Rapamycin Treatment Reduces Fibrogenesis, Improves Liver Function, and Prolongs Survival in Rats with Established Liver Cirrhosis." *Journal of Hepatology*, vol. 45, No. 6, 2006, pp. 786-796.
Patsenker, Eleonora, et al., "Potent Antifibrotic Activity of MTOR Inhibitors Sirolimus and Everolimus but Not of Cyclosporine A and Tacrolimus in Experimental Liver Fibrosis." *Journal of Hepatology*, vol. 55, No. 2, 2011, pp. 388-398.
Extended search report for European Patent Application No. 16839531.7, dated Dec. 17, 2018.
Chemical Abstract compound, STN express. RN 1276633-44-3 Registry (Entered STN: Apr. 7, 2011).
Chemical Abstract compound, STN express. RN 1225851-09-1 Registry (Entered STN: May 30, 2010).
Chemical Abstract compound, STN express. RN 1390517-03-9 Registry (Entered STN: Aug. 13, 2012).
Chemical Abstract compound, STN express. RN 1301674-36-1 Registry (Entered STN: May 27, 2011).
Chemical Abstract compound, STN express. RN 1294575-92-0 Registry (Entered STN: May 15, 2011).
Office Action for Korean Patent Application No. 10-2015-0118247, dated Jun. 26, 2019.
Chemical Abstract compound, STN express. RN 69202-22-89 Registry (Entered STN: Nov. 16, 1984).
Office Action for Chinese Patent Application No. 201680046879.0, dated Jan. 6, 2020.

* cited by examiner

CATECHOL DERIVATIVE AND PHARMACEUTICAL COMPOSITION COMPRISING THE SAME

CROSS-REFERENCE TO RELATED APPLICATIONS

This application is a National Phase Application of PCT International Application No. PCT/KR2016/009196, International Filing Date Aug. 19, 2016, claiming priority of Korean Patent Application No. 10-2015-0118247, filed Aug. 21, 2015, which is hereby incorporate by reference in its entirety.

TECHNICAL FIELD

The present invention relates to a novel catechol derivative and a pharmaceutical composition comprising the same. The catechol derivative according to the present invention can be usefully used for the prevention and treatment of liver diseases.

BACKGROUND ART

Liver fibrosis is a common healing response to chronic liver injury of all causes. In order to heal injured tissues, liver tissue deposits new collagen in the wound, but over time, such a process leads to liver cirrhosis. Liver fibrosis is usually associated with chronic liver diseases caused by infections, drugs, metabolic disorders, or autoimmune imbalances. Liver fibrosis caused by the parenchymal cell death and necrosis over a long period of time is associated with inflammatory response, which invites immune cells, activates and accumulates fibrogenic cells, and induces extracellular matrix accumulation. Progression of fibrosis due to continuous liver injury is associated with the expansion of the fibrotic septa and ultimately causes liver cirrhosis.

Liver fibrosis can develop into liver cirrhosis between 1 and 10 years and increases a 7- to 10-year liver-related mortality causes from 12% to 25% (Farrell, G. C. & Larter, C. Z. Nonalcoholic fatty liver disease: from steatosis to cirrhosis. *Hepatology* 43, S99-S112 (2006)). Unfortunately, however, effective clinical therapies are still lacking. Therefore, effective anti-fibrosis therapies are good targets for the treatment of liver diseases. Currently, anti-fibrosis strategies targeting various stages leading to liver fibrosis have been recognized. That is, there are methods of inhibiting the apoptosis of liver cells, or inhibiting liver inflammation, or promoting the apoptosis of fibrogenic cells, or returning phenotype fibrogenic cells to a quiescent state. However, specific drugs used to treat liver fibrosis so far are still limited.

Meanwhile, autophagy is a process by which eukaryotic cells digest their own cellular organs and long lived proteins as a kind of metabolic process. The process is closely associated with cell growth, differentiation and homeostasis. Further, the process is the only way to digest "long lived" or "broken" cell organs (Klionsky, D. J. & Emr, S. D. Autophagy as a regulated pathway of cellular degradation. *Science* 290, 1717-1721 (2000), Levine, B. & Klionsky, D. J. Development by self-digestion: molecular mechanisms and biological functions of autophagy. *Developmental cell* 6, 463-477 (2004)). Autophagy acts as an important regulator of liver homeostasis under physiological and pathological conditions (Codogno, P. & Meijer, A. J. Autophagy in the liver. *Journal of hepatology* 59, 389-391 (2013). Rautou, P.-E. et al. Autophagy in liver diseases. *Journal of hepatology* 53, 1123-1134 (2010). Czaja, M. J. et al. Functions of autophagy in normal and diseased liver. *Autophagy* 9, 1131-1158 (2013)). Currently, autophagy has been recognized as an important pathway for regulating the supply of substrate required for homeostasis and energy production by selectively targeting specific components in cells such as aggregated protein, damaged/excess organelles, and lipids and then degrading them through lysosomal pathway (Autophagy. 2013 August; 9(8); 1131-58). Recent studies have also shown that autophagy is one new regulatory pathway related to liver fibrosis. Autophagy directly contributes to the activation process of hepatic stellate cells (HSCs) inducing hepatic fibrosis, or possibly promotes liver fibrosis by indirect action on other fibrogenic cells.

The liver, which is also a representative model of autophagy research, is characterized by: 1) very excellent reproducibility; 2) an important metabolic organ; and 3) an organ that is exposed to infection by liver trophic virus. Therefore, the core functions of the organ such as regeneration, metabolism, and immunity are closely related to autophagy (Autophagy. 2013 August; 9 (8): 1131-58). Liver ischemia-reperfusion occurs clinically during liver transplantation, trauma, shock, and elective liver resection.

During ischemia-reoxygenation, ROS (reactive oxygen species) and $Ca^{2+}$ levels increase inside mitochondria, which causes mitochondria permeability transition, and oxidative phosphorylation is uncoupled, ultimately inducing apoptosis along with depletion of energy and ATP. Because autophagy proteins are inhibited during anoxia/reoxygenation, the damaged mitochondria are not removed. Therefore, a strategy to activate tolerance to ischemia-reperfusion by activating autophagy has been attempted in preclinical models. Meanwhile, in the acute liver injury model, autophagy is activated to increase cell survival in stress situations.

PI3K/AKT/mTOR signaling pathway regulates various cellular processes such as cell growth or proliferation, motility, survival, apoptosis, protein synthesis and transcription (Hay, N. & Sonenberg, N. Upstream and downstream of mTOR. *Genes & development* 18, 1926-1945 (2004). Yang, Q. & Guan, K.-L. Expanding mTOR signaling. *Cell research* 17, 666-681 (2007). Schmelzle, T. & Hall, M. N. TOR, a central controller of cell growth. *Cell* 103, 253-262 (2000). Sarbassov, d. D., Ali, S. M. & Sabatini, D. M. Growing roles for the mTOR pathway. *Current opinion in cell biology* 17, 596-603 (2005)). Further, the PI3K/AKT/mTOR signaling pathway is well known as a major pathway in autophagy. If mTOR signaling is inhibited due to lack of nutrition and growth factors, autophagy is induced. On the contrary, when nutrition and growth factors are abundant, mTORC1 is activated, thereby inhibiting autophagy through ULK1 complex and promoting cell growth and metabolic activity. Many experimental data reported that the AKT/mTOR signaling pathway is at the center of HSCs activation (Reif, S. et al. The role of focal adhesion kinase-phosphatidylinositol 3-kinase-akt signaling in hepatic stellate cell proliferation and type I collagen expression. *Journal of Biological Chemistry* 278, 8083-8090 (2003). Gabele, E. et al. The role of p70S6K in hepatic stellate cell collagen gene expression and cell proliferation. *Journal of Biological Chemistry* 280, 13374-13382 (2005). Gabele, E., Brenner, D. A. & Rippe, R. A. Liver fibrosis: signals leading to the amplification of the fibrogenic hepatic stellate cell. *Front Biosci* 8, 69-d77 (2003)). Inhibition of mTOR signaling pathway by mTOR inhibitor Rapamycin has been reported to reduce fibrous tissue growth, improve liver function and reduce portal pressure in animal models of liver cirrhosis (Biecker, E. et al. Long-term treatment of bile duct-ligated rats with rapamycin (sirolimus) significantly attenuates liver fibrosis: analysis of the underlying mechanisms. *Journal of Pharmacology and Experimental Therapeutics* 313, 952-961 (2005). Neef, M., Ledermann, M., Saegesser, H., Schneider, V. & Reichen, J. Low-dose oral rapamycin treatment reduces fibrogenesis, improves liver function, and prolongs survival in rats with established liver cirrhosis. *Journal of hepatology* 45, 786-796 (2006). Patsenker, E. et al. Potent antifibrotic activity of mTOR inhibitors sirolimus and everolimus but not of cyclosporine A and tacrolimus in experimental liver fibrosis. *Journal of hepatology* 55, 388-398 (2011)). In addition, Rapamycin is used as a primary immunosuppressive agent in liver transplant patients, and Sirolimus and Everolimus, which are mTOR inhibitors, have been reported to reduce fibrosis progression and portal hypertension under experimental conditions.

Therefore, the present inventors have learned from the above-mentioned prior studies that autophagy plays a crucial role in liver diseases, and based on the findings, the inventors have conducted intensive studies to develop a compound that can induce activity of autophagy. As a result, the inventors have found that novel catechol derivatives as described below have excellent effects for activating autophagy and activities for inhibiting liver diseases, thereby completing the present invention.

DETAILED DESCRIPTION OF THE INVENTION

Technical Problem

It is an object of the present invention to provide a novel catechol derivative and a pharmaceutical composition comprising the same. It is another object of the present invention to provide a method for preparing the above-mentioned catechol derivative.

Technical Solution

In order to solve the objects mentioned above, the present invention provides a compound represented by Chemical Formula 1 below, or a pharmaceutically acceptable salt thereof:

[Chemical Formula 1]

in Chemical Formula 1, $R_1$ and $R_2$ are each independently $C_{1-4}$ alkyl, or $R_1$ and $R_2$ are connected together to form $C_{1-4}$ alkylene, $R_3$ is $C_{1-4}$ alkyl, $C_{1-4}$ alkyl substituted with $C_{5-10}$ heteroaryl, $C_{6-10}$ aryl, or $C_{5-10}$ heteroaryl, X is CH, or N, and Y is NH, or O.

Preferably, $R_1$ and $R_2$ are methyl or $R_1$ and $R_2$ are connected together to form methylene (—$CH_2$—) or ethylene (—$CH_2$—$CH_2$—).

Further, preferably, the $C_{6-10}$ aryl included in the definition of $R_3$ is phenyl and the $C_{5-10}$ heteroaryl is pyridine. More preferably, $R_3$ is methyl, ethyl, isopropyl, isobutyl, pyridinylmethyl, phenyl, or pyridine.

Further, preferably, $R_1$ and $R_2$ are each independently $C_{1-4}$ alkyl, or $R_1$ and $R_2$ are connected together to form $C_{1-4}$ alkylene; $R_3$ is $C_{1-4}$ alkyl, $C_{1-4}$ alkyl substituted with $C_{5-10}$ heteroaryl, $C_{6-10}$ aryl, or $C_{5-10}$ heteroaryl; X is CH; and Y is NH.

Further, preferably, $R_1$ and $R_2$ are connected together to form $C_{1-4}$ alkylene; $R_3$ is $C_{1-4}$ alkyl, or $C_{6-10}$ aryl; X is N; and Y is NH.

Further, preferably, $R_1$ and $R_2$ are methyl, or $R_1$ and $R_2$ are connected together to form methylene; $R_3$ is isopropyl, isobutyl, or phenyl; X is CH; and Y is NH.

Representative examples of the compound represented by Chemical Formula 1 are as follows:
1) 5-(3,4-dimethoxyphenyl)-N-isopropylthiophene-2-carboxamide,
2) 5-(benzo[d][1,3]dioxol-5-yl)-N-isopropylthiophene-2-carboxamide,
3) 5-(2,3-dihydrobenzo[b][1,4]dioxin-6-yl)-N-isopropylthiophene-2-carboxamide,
4) 5-(3,4-dimethoxyphenyl)-N-isobutylthiophene-2-carboxamide,
5) 5-(benzo[d][1,3]dioxol-5-yl)-N-isobutylthiophene-2-carboxamide,
6) 5-(2,3-dihydrobenzo[b][1,4]dioxin-6-yl)-N-isobutylthiophene-2-carboxamide,
7) 5-(3,4-dimethoxyphenyl)-N-phenylthiophene-2-carboxamide,
8) 5-(benzo[d][1,3]dioxol-5-yl)-N-phenylthiophene-2-carboxamide,
9) 5-(2,3-dihydrobenzo[b][1,4]dioxin-6-yl)-N-phenylthiophene-2-carboxamide,
10) 5-(benzo[d][1,3]dioxol-5-yl)-N-(pyridin-2-yl)thiophene-2-carboxamide,
11) 5-(benzo[d][1,3]dioxol-5-yl)-N-(pyridin-2-ylmethyl)thiophene-2-carboxamide,
12) 5-(2,3-dihydrobenzo[b][1,4]dioxin-6-yl)-N-(pyridin-2-ylmethyl)thiophene-2-carboxamide,
13) 2-(benzo[d][1,3]dioxol-5-yl)-N-isopropylthiazole-5-carboxamide,
14) 2-(2,3-dihydrobenzo[b][1,4]dioxin-6-yl)-N-isopropylthiazole-5-carboxamide,
15) 2-(benzo[d][1,3]dioxol-5-yl)-N-isobutylthiazole-5-carboxamide,
16) 2-(2,3-dihydrobenzo[b][1,4]dioxin-6-yl)-N-isobutylthiazole-5-carboxamide,
17) 2-(benzo[d][1,3]dioxol-5-yl)-N-phenylthiazole-5-carboxamide,
18) 2-(2,3-dihydrobenzo[b][1,4]dioxin-6-yl)-N-phenylthiazole-5-carboxamide,
19) methyl 5-(benzo[d][1,3]dioxol-5-yl)thiophene-2-carboxylate, and
20) ethyl 2-(benzo[d][1,3]dioxol-5-yl)thiazole-5-carboxylate.

In addition, if necessary, the compound represented by Chemical Formula 1 can be prepared in the form of a pharmaceutically acceptable salt using conventional methods in the technical field to which the present invention pertains. For example, a pharmaceutically acceptable metal salt can be obtained using a base by a conventional method, and examples of the metal salt include a sodium salt, a potassium salt, or a calcium salt. In another example, an acid addition salt formed by a pharmaceutically acceptable free acid is useful. As the free acid, an inorganic acid and an organic acid can be used. As the inorganic acid, hydrochloric acid, bromic acid, sulfuric acid, phosphoric acid and the like can be used. As the organic acid, citric acid, acetic acid, lactic acid, maleic acid, gluconic acid, methanesulfonic acid, succinic acid, 4-toluenesulfonic acid, glutamic acid, aspartic acid, or the like can be used.

The compound represented by Chemical Formula 1 according to the present invention includes not only pharmaceutically acceptable salts thereof, but also solvates and hydrates that can be prepared therefrom. The solvates and hydrates of the compound represented by Chemical Formula 1 can be prepared from the compound represented by Chemical Formula 1 using a conventional method in the technical field to which the present invention pertains.

In addition, the compound represented by Chemical Formula 1 according to the present invention may be prepared either in a crystalline form or in a non-crystalline form, and when the compound of Chemical Formula 1 is prepared in a crystalline form, it may be optionally hydrated or solvated. In the present invention, the compound of Chemical Formula 1 may not only include a stoichiometric hydrate, but also include a compound containing various amounts of water. The solvate of the compound of Chemical Formula 1 according to the present invention includes both stoichiometric solvates and non-stoichiometric solvates.

The present invention also provides a method for preparing a compound represented by Chemical Formula 1, comprising reacting a compound represented by Chemical Formula 2 below and a compound represented by Chemical Formula 3 below to prepare a compound represented by Chemical Formula 1, as shown in Reaction Scheme 1 below:

[Reaction Scheme 1]

in Reaction Scheme 1, $R_1$, $R_2$, $R_3$, X and Y are as previously defined, and $R_4$ is halogen. Preferably, $R_4$ is chloro, or bromo.

The reaction is preferably carried out in the presence of sodium carbonate, and palladium (II) acetate. Also, the reaction molar ratio between the compound represented by Chemical Formula 2 and the compound represented by Chemical Formula 3 is preferably 10:1 to 10:1. Further, as the solvent for the reaction, 1,2-dimethoxyethane, water, or a mixed solvent thereof is preferably used. In addition, the reaction is preferably carried out under microwave irradiation at a temperature of 20° C. to 200° C., and it is desirable to perform ultrasonic treatment concurrently during the reaction. Further, the reaction is preferably carried out for 10 minutes to 10 hours. After the reaction, a purification process may be included if necessary.

Further, the present invention provides a pharmaceutical composition for preventing or treating autophagy-related diseases, comprising the compound represented by Chemical Formula 1 or a pharmaceutically acceptable salt thereof. In addition, the present invention provides a compound represented by Chemical Formula 1, or a pharmaceutically acceptable salt thereof, which is used to prevent or treat autophagy-related diseases. Further, the present invention provides a method for preventing or treating autophagy-related diseases in a subject in need thereof, comprising administering a compound represented by Chemical Formula 1, or a pharmaceutically acceptable salt thereof to a subject that has or is suspected of having autophagy-related diseases.

The compound represented by Chemical Formula 1 according to the present invention, or a pharmaceutically acceptable salt thereof can increase the autophagy activity and thus can be usefully used for the prevention or treatment of autophagy-related diseases. Examples of the autophagy-related diseases include liver diseases. Examples of the liver diseases include liver fibrosis, liver cirrhosis, hepatitis, alcoholic liver disease, fatty liver, or non-alcoholic steatohepatitis (NASH).

As used herein, the term "prevention" refers to any act to delay or inhibit occurrence, spread or recurrence of the autophagy-related diseases by administration of the composition of the present invention, and the term "treatment" refers to any act to improve or change the symptoms of the above diseases for the better by administration of the composition of the present invention.

The pharmaceutical composition according to the present invention can be formulated in types for oral or parenteral administrations according to a standard pharmaceutical practice. These formulations may contain additives such as pharmaceutically acceptable carrier, adjuvant or diluent in addition to the active ingredient. Suitable carriers include, for example, physiological saline, polyethylene glycol, ethanol, vegetable oil, isopropyl myristate and the like. Diluents include, for example, lactose, dextrose, sucrose, mannitol, sorbitol, cellulose and/or glycine and the like, but are not limited thereto. Further, the compounds of the present invention can be dissolved in oils, propylene glycol or other solvents commonly used in the preparation of injection solutions. Furthermore, the compounds of the present invention can be formulated in ointments or creams for topical application.

A preferred dose of the compound of the present invention may be varied according to the condition and weight of a patient, the severity of a disease, the type of a drug, and the route and duration of administration, but it may be suitably selected by those skilled in the art. In order to achieve the desirable effects, however, the compound represented by Chemical Formula 1 according to the present invention may be administrated daily at a dose of 0.0001 to 100 mg/kg (body weight), and preferably 0.001 to 100 mg/kg (body weight). The administration may be performed once a day or in divided doses each day through an oral or parenteral route.

Depending on the method of administration, the pharmaceutical composition according to the present invention may contain the compound represented by Chemical Formula 1 according to the present invention or a pharmaceutically acceptable salt thereof in an amount of 0.001 to 99% by weight, preferably 0.01 to 60% by weight.

The pharmaceutical composition of the present invention may be administered to mammals such as a rat, a mouse, a domestic animal and a human, through various routes. The administration may be carried out through all possible methods, for example, oral, rectal, intravenous, intramuscular, subcutaneous, intra-endometrial, intracerebroventricular injection.

Advantageous Effects

The compound according to the present invention or a pharmaceutically acceptable salt thereof exhibits effects for activating autophagy and activities for inhibiting liver diseases, and thus can be usefully used for the prevention or treatment of autophagy-related diseases.

DETAILED DESCRIPTION OF THE EMBODIMENTS

Below, the present invention will be described in more detail by way of examples. However, these examples are provided for illustrative purposes only, and should not be construed as limiting the scope of the present invention to these examples.

Example 1: Preparation of 5-(3,4-dimethoxyphenyl)-N-isopropylthiophene-2-carboxamide 5-Chloro-N-isopropylthiophene-2-carboxamide (2.015 mmol), 3,4-dimethoxyphenylboronic acid (3.022 mmol), sodium carbonate (1281.4 mg, 12.09 mmol) and palladium (II) acetate (27.56 mg, 0.05 mmol) were added to 1,2-dimethoxyethane (8 mL) and double distilled water (2 mL), and the mixture was stirred at 120° C. for 200 minutes together with ultrasonic treatment and then extracted three times with dichloromethane. The extracted solution was dried over anhydrous magnesium sulfate. The organic solvent was concentrated under reduced pressure, purified by flash column chromatography (n-Hx: EtOAc=3:1) and then dried by a vacuum pump to give the title compound as a white solid (yield: 66.70%).

$^1$H NMR (400 MHz, DMSO-d6) δ 8.18 (d, 1H, J=7.8 Hz), 7.73 (d, 1H, J=3.9 Hz), 7.42 (d, 1H, J=3.9 Hz), 7.24-7.17 (m, 2H), 6.98 (d, 1H, J=8.3 Hz), 4.10-3.97 (m, 1H), 3.82 (s, 3H), 3.77 (s, 3H), 1.15 (d, 6H, J=6.6 Hz); $^{13}$C NMR (100 MHz, DMSO-d6) δ 160.5, 149.6, 149.5, 147.9, 138.6, 129.2, 126.5, 123.5, 118.6, 112.6, 109.6, 56.0, 56.0, 41.4, 22.8, 22.8; ESI (m/z) 306 (MH$^+$)

Example 2: Preparation of 5-(benzo[d][1,3]dioxol-5-yl)-N-isopropylthiophene-2-carboxamide 5-Chloro-N-isopropylthiophene-2-carboxamide (2.015 mmol), benzo[d][1,3]dioxol-5-ylboronic acid (3.022 mmol), sodium carbonate (1281.4 mg, 12.09 mmol) and palladium (II) acetate (27.56 mg, 0.05 mmol) were added to 1,2-dimethoxyethane (8 mL) and double distilled water (2 mL), and the mixture was stirred at 120° C. for 200 minutes together with ultrasonic treatment and then extracted three times with dichloromethane. The extracted solution was dried over anhydrous magnesium sulfate. The organic solvent was concentrated under reduced pressure, purified by flash column chromatography (n-Hx: EtOAc=3:1) and then dried by a vacuum pump to give the title compound as a brown solid (yield: 64.41%).

¹H NMR (400 MHz, DMSO-d6) δ 8.19 (d, 1H, J=7.7 Hz), 7.70 (d, 1H, J=3.9 Hz), 7.38 (d, 1H, J=3.9 Hz, 1H), 7.27 (d, 1H, J=1.7 Hz), 7.16 (dd, 1H, $J_A$=8.1 Hz, $J_B$=1.7 Hz), 6.94 (d, 1H, J=8.1 Hz), 6.05 (s, 2H), 4.07-3.99 (m, 1H), 1.14 (d, 6H, J=6.6 Hz); ¹³C NMR (100 MHz, DMSO-d6) δ 160.5, 148.5, 147.9, 147.5, 138.9, 129.1, 127.9, 123.8, 120.0, 109.2, 106.4, 101.8, 41.4, 22.8, 22.8; ESI (m/z) 290 (MH⁺)

Example 3: Preparation of 5-(2,3-dihydrobenzo[b][1,4]dioxin-6-yl)-N-isopropylthiophene-2-carboxamide 5-Chloro-N-isopropylthiophene-2-carboxamide (2.015 mmol), 2,3-dihydrobenzo[b][1,4]dioxin-6-yldiboric acid (3.022 mmol), sodium carbonate (1281.4 mg, 12.09 mmol) and palladium (II) acetate (27.56 mg, 0.05 mmol) were added to 1,2-dimethoxyethane (8 mL) and double distilled water (2 mL), and the mixture was stirred at 120° C. for 200 minutes together with ultrasonic treatment and then extracted three times with dichloromethane. The extracted solution was dried over anhydrous magnesium sulfate. The organic solvent was concentrated under reduced pressure, purified by flash column chromatography (n-Hx: EtOAc=3:1) and then dried by a vacuum pump to give the title compound as a white solid (yield: 45.52%).

¹H NMR (400 MHz, DMSO-d6) δ 8.18 (d, 1H, J=7.7 Hz), 7.70 (d, 1H, J=3.9 Hz), 7.36 (d, 1H, J=3.9 Hz), 7.18-7.09 (m, 2H), 6.89 (d, 1H, J=8.3 Hz), 4.25 (s, 4H), 4.10-3.97 (m, 1H), 1.14 (d, 5H, J=6.6 Hz); ¹³C NMR (100 MHz, DMSO-d6) δ 160.5, 147.3, 144.2, 144.1, 138.8, 129.2, 127.1, 123.6, 119.2, 118.1, 114.5, 64.6, 64.5, 41.47, 22.8, 22.8; ESI (m/z) 304 (MH⁺)

Example 4: Preparation of 5-(3,4-dimethoxyphenyl)-N-isobutylthiophene-2-carboxamide The title compound (yield: 55.01%) was obtained as a yellow solid in the same manner as in Example 1, except that 5-chloro-N-isobutylthiophene-2-carboxamide was used instead of 5-chloro-N-isopropylthiophene-2-carboxamide.

¹H NMR (400 MHz, DMSO-d6) δ 8.42 (t, 1H, J=5.8 Hz), 7.72 (d, 1H, J=3.9 Hz), 7.42 (d, 1H, J=3.9 Hz), 7.23-7.17 (m, 2H), 6.98 (d, 1H, J=8.1 Hz), 3.82 (s, 3H), 3.77 (s, 3H), 3.04 (t, 2H, J=6.4 Hz), 1.87-1.73 (m, 1H), 0.87 (d, 6H, J=6.7 Hz); ¹³C NMR (100 MHz, DMSO-d6) δ 161.4, 149.6, 149.5, 147.9, 138.5, 129.2, 126.5, 123.6, 118.7, 112.6, 109.7, 56.0, 56.0, 47.0, 28.6, 20.6, 20.6; ESI (m/z) 320 (MH⁺)

Example 5: Preparation of 5-(benzo[d][1,3]dioxol-5-yl)-N-isobutylthiophene-2-carboxamide The title compound (yield: 37.68%) was obtained as a white solid in the same manner as in Example 2, except that 5-chloro-N-isobutylthiophene-2-carboxamide was used instead of 5-chloro-N-isopropylthiophene-2-carboxamide.

¹H NMR (400 MHz, DMSO-d6) δ 8.43 (t, 1H, J=5.7 Hz), 7.70 (d, 1H, J=3.8 Hz), 7.38 (d, 1H, J=3.8 Hz), 7.27 (s, 1H), 7.15 (d, 1H, J=8.0 Hz), 6.95 (d, 1H, J=8.1 Hz), 6.05 (s, 2H), 3.04 (t, 2H, J=6.4 Hz), 1.91-1.74 (m, 1H), 0.87 (d, 6H, J=6.7 Hz); ¹³C NMR (100 MHz, DMSO-d6) δ 161.4, 148.5, 147.9, 147.5, 138.7, 129.1, 127.9, 123.9, 120.1, 109.2, 106.4, 101.8, 47.0, 28.6, 20.6, 20.6; ESI (m/z) 304 (MH⁺)

Example 6: Preparation of 5-(2,3-dihydrobenzo[b][1,4]dioxin-6-yl)-N-isobutylthiophene-2-carboxamide The title compound (yield: 37.11%) was obtained as a white solid in the same manner as in Example 3, except that 5-chloro-N-isobutylthiophene-2-carboxamide was used instead of 5-chloro-N-isopropylthiophene-2-carboxamide.

¹H NMR (400 MHz, DMSO-d6) δ 8.42 (t, 1H, J=5.6 Hz), 7.70 (d, 1H, J=3.8 Hz), 7.36 (d, 1H, J=3.8 Hz), 7.16 (s, 1H), 7.13 (d, 1H, J=8.4 Hz), 6.89 (d, 1H, J=8.3 Hz), 4.25 (s, 4H), 3.04 (t, 2H, J=6.3 Hz), 1.89-1.72 (m, 1H), 0.87 (d, 6H, J=6.6 Hz); ¹³C NMR (100 MHz, DMSO-d6) δ 161.4, 147.3, 144.2, 144.1, 138.7, 129.2, 127.1, 123.7, 119.3, 118.1, 114.5, 64.6, 64.5, 47.0, 28.6, 20.6, 20.6; ESI (m/z) 318 (MH⁺)

Example 7: Preparation of 5-(3,4-dimethoxyphenyl)-N-phenylthiophene-2-carboxamide The title compound (yield: 66.53%) was obtained as a yellow solid in the same manner as in Example 1, except that 5-chloro-N-phenylthiophene-2-carboxamide was used instead of 5-chloro-N-isopropylthiophene-2-carboxamide.

$^1$H NMR (400 MHz, DMSO-d6) δ 10.18 (s, 1H), 7.99 (d, 1H, J=3.9 Hz), 7.73 (d, 2H, J=8.0 Hz), 7.53 (d, 1H, J=3.9 Hz), 7.34 (t, 2H, J=7.8 Hz), 7.28-7.22 (m, 2H), 7.08 (t, 1H, J=7.3 Hz), 7.00 (d, 1H, J=8.3 Hz), 3.84 (s, 3H), 3.78 (s, 3H); $^{13}$C NMR (100 MHz, DMSO-d6) δ 160.1, 149.8, 149.5, 149.3, 139.2, 138.1, 130.6, 129.1, 129.1, 126.3, 124.1, 123.8, 120.7, 120.7, 118.8, 112.5, 109.7, 56.0, 56.0; ESI (m/z) 340 (MH$^+$), 362 (MN$^+$)

Example 8: Preparation of 5-(benzo[d][1,3]dioxol-5-yl)-N-phenylthiophene-2-carboxamide The title compound (yield: 15.66%) was obtained as a white solid in the same manner as in Example 2, except that 5-chloro-N-phenylthiophene-2-carboxamide was used instead of 5-chloro-N-isopropylthiophene-2-carboxamide.

$^1$H NMR (400 MHz, DMSO-d6) δ 10.18 (s, 1H), 7.97 (d, 1H, J=3.9 Hz), 7.72 (d, 2H, J=7.8 Hz), 7.49 (d, 1H, J=3.9 Hz), 7.40-7.28 (m, 3H), 7.22 (dd, 1H, J$_A$=8.1 Hz, J$_B$=1.6 Hz), 7.09 (t, 1H, J=7.3 Hz), 6.97 (d, 1H, J=8.1 Hz), 6.07 (s, 2H); ESI (m/z) 346 (MNa$^+$)

Example 9: Preparation of 5-(2,3-dihydrobenzo[b][1,4]dioxin-6-yl)-N-phenylthiophene-2-carboxamide The title compound (yield: 44.53%) was obtained as a white solid in the same manner as in Example 3, except that 5-chloro-N-phenylthiophene-2-carboxamide was used instead of 5-chloro-N-isopropylthiophene-2-carboxamide.

$^1$H NMR (400 MHz, DMSO-d6) δ 10.18 (s, 1H), 7.97 (d, 1H, J=3.7 Hz), 7.72 (d, 2H, J=8.0 Hz), 7.47 (d, 1H, J=3.7 Hz), 7.34 (t, 2H, J=7.7 Hz), 7.22 (s, 1H), 7.19 (d, 1H, J=8.4 Hz), 7.08 (t, 1H, J=7.2 Hz), 6.91 (d, 1H, J=8.3 Hz), 4.26 (s, 4H); $^{13}$C NMR (100 MHz, DMSO-d6) δ 160.1, 148.7, 144.4, 144.1, 139.1, 138.3, 130.6, 129.1, 129.1, 126.8, 124.1, 123.9, 120.7, 120.7, 119.4, 118.2, 114.7, 64.6, 64.5; ESI (m/z) 338 (MH$^+$), 360 (MNa$^+$)

Example 10: Preparation of 5-(benzo[d][1,3]dioxol-5-yl)-N-(pyridin-2-yl)thiophene-2-carboxamide The title compound (yield: 13.54%) was obtained as a yellow solid in the same manner as in Example 2, except that 5-chloro-N-(pyridin-2-yl)thiophene-2-carboxamide was used instead of 5-chloro-N-isopropylthiophene-2-carboxamide.

$^1$H NMR (400 MHz, DMSO-d6) δ 10.86 (s, 1H), 8.37 (d, 1H, J=4.6 Hz), 8.18 (d, 1H, J=4.0 Hz), 8.13 (d, 1H, J=8.4 Hz), 7.81 (t, 1H, J=7.8 Hz), 7.47 (d, 1H, J=3.9 Hz), 7.34 (s, 1H), 7.22 (d, 1H, J=8.1 Hz), 7.14 (t, 1H, J=7.6 Hz), 6.97 (d, 1H, J=8.1 Hz), 6.07 (s, 2H); $^{13}$C NMR (100 MHz, DMSO-d6) δ 160.6, 152.3, 149.6, 148.5, 148.3, 148.2, 138.6, 137.7, 131.6, 127.6, 124.4, 120.4, 120.1, 115.0, 109.3, 106.5, 101.9; ESI (m/z) 325 (MH$^+$), 347 (MNa$^+$)

Example 11: Preparation of 5-(benzo[d][1,3]dioxol-5-yl)-N-(pyridin-2-ylmethyl)thiophene-2-carboxamide The title compound (yield: 24.12%) was obtained as a white solid in the same manner as in Example 2, except that 5-chloro-N-(pyridin-2-ylmethyl)thiophene-2-carboxamide was used instead of 5-chloro-N-isopropylthiophene-2-carboxamide.

$^1$H NMR (400 MHz, DMSO-d6) δ 9.12 (t, 1H, J=5.9 Hz), 8.50 (d, 1H, J=4.2 Hz), 7.78 (d, 1H, J=3.9 Hz), 7.75 (td, 1H, J$_A$=7.8 Hz, J$_B$=1.7 Hz), 7.42 (d, 1H, J=3.9 Hz), 7.35-7.29 (m, 2H), 7.25 (dd, 1H, J$_A$=7.0 Hz, J$_B$=5.2 Hz), 7.18 (dd, 1H, J$_A$=8.1 Hz, J$_B$=1.7 Hz), 6.96 (d, 1H, J=8.1 Hz), 6.06 (s, 2H), 4.53 (d, 2H, J=6.0 Hz); $^{13}$C NMR (400 MHz, DMSO-d6) δ 161.6, 159.0, 149.3, 148.5, 148.0, 148.0, 138.0, 137.2, 129.7, 127.8, 124.1, 122.6, 121.5, 120.2, 109.3, 106.5, 101.9, 44.9; ESI (m/z) 339 (MH$^+$)

Example 12: Preparation of 5-(2,3-dihydrobenzo[b][1,4]dioxin-6-yl)-N-(pyridin-2-ylmethyl)thiophene-2-carboxamide The title compound (yield: 59.09%) was obtained as a white solid in the same manner as in Example 3, except that 5-chloro-N-(pyridin-2-ylmethyl)thiophene-2-carboxamide was used instead of 5-chloro-N-isopropylthiophene-2-carboxamide.

$^{1}$H NMR (400 MHz, DMSO-d6) δ 9.11 (t, 1H, J=6.0 Hz), 8.50 (d, 1H, J=4.2 Hz), 7.78 (d, 1H, J=3.9 Hz), 7.75 (td, 1H, $J_{A}$=7.8 Hz, $J_{B}$=1.7 Hz), 7.40 (d, 1H, J=3.9 Hz), 7.31 (d, 1H, J=7.8 Hz), 7.25 (dd, 1H, $J_{A}$=7.1 Hz, $J_{B}$=5.1 Hz), 7.19 (d, 1H, J=2.1 Hz), 7.15 (dd, 1H, $J_{A}$=8.4 Hz, $J_{B}$=2.2 Hz), 6.90 (d, 1H, J=8.4 Hz), 4.53 (d, 2H, J=6.0 Hz), 4.26 (s, 4H); $^{13}$C NMR (100 MHz, DMSO-d6) δ 161.6, 159.0, 149.3, 147.8, 144.3, 144.1, 138.0, 137.2, 129.7, 127.0, 123.9, 122.6, 121.5, 119.3, 118.2, 114.6, 64.6, 64.5, 44.9; ESI (m/z) 353 (MH$^{+}$)

Example 13: Preparation of 2-(benzo[d][1,3]dioxol-5-yl)-N-Isopropylthiazole-5-carboxamide The title compound (yield: 66.33%) was obtained as a yellow solid in the same manner as in Example 2, except that 2-chloro-N-isopropylthiazole-5-carboxamide was used instead of 5-chloro-N-isopropylthiophene-2-carboxamide.

$^{1}$H NMR (400 MHz, DMSO-d6) δ 8.41 (d, 1H, J=7.6 Hz), 8.35 (s, 1H), 7.51-7.44 (m, 2H), 7.01 (d, 1H, J=8.1 Hz), 6.10 (s, 2H), 4.10-3.96 (m, 1H), 1.15 (d, 6H, J=6.6 Hz); $^{13}$C NMR (100 MHz, DMSO-d6) δ 169.9, 159.2, 150.0, 148.5, 143.8, 135.5, 127.4, 121.8, 109.3, 106.5, 102.3, 41.6, 22.7, 22.7; ESI (m/z) 291 (MH$^{+}$)

Example 14: Preparation of 2-(2,3-dihydrobenzo[b][1,4]dioxin-6-yl)-N-Isopropylthiazole-5-carboxamide The title compound (yield: 65.40%) was obtained as a white solid in the same manner as in Example 3, except that 2-chloro-N-isopropylthiazole-5-carboxamide was used instead of 5-chloro-N-isopropylthiophene-2-carboxamide.

$^{1}$H NMR (400 MHz, DMSO-d6) δ 8.41 (d, 1H, J=7.6 Hz), 8.35 (s, 1H), 7.44-7.40 (m, 2H), 6.95 (d, 1H, J=7.9 Hz), 4.28 (s, 4H), 4.13-3.94 (m, 1H), 1.15 (d, 6H, J=6.6 Hz); $^{13}$C NMR (100 MHz, DMSO-d6) δ 169.8, 159.3, 146.3, 144.1, 143.9, 135.5, 126.5, 120.3, 118.2, 115.2, 64.8, 64.5, 41.6, 22.7, 22.7; ESI (m/z) 305 (MH$^{+}$)

Example 15: Preparation of 2-(benzo[d][1,3]dioxol-5-yl)-N-Isobutylthiazole-5-carboxamide The title compound (yield: 58.92%) was obtained as a white solid in the same manner as in Example 2, except that 2-chloro-N-isopropylthiazole-5-carboxamide was used instead of 5-chloro-N-isopropylthiophene-2-carboxamide.

$^{1}$H NMR (400 MHz, DMSO-d6) δ 8.64 (t, 1H, J=5.8 Hz), 8.36 (s, 1H), 7.53-7.45 (m, 2H), 7.01 (d, 1H, J=8.1 Hz), 6.10 (s, 2H), 3.05 (t, 2H, J=6.4 Hz), 1.88-1.70 (m, 1H), 0.87 (d, 6H, J=6.7 Hz); $^{13}$C NMR (100 MHz, DMSO-d6) δ 170.0, 160.1, 150.0, 148.5, 143.8, 135.3, 127.4, 121.8, 109.3, 106.5, 102.3, 47.0, 28.6, 20.6, 20.6; ESI (m/z) 305 (MH$^{+}$)

Example 16: Preparation of 2-(2,3-dihydrobenzo[b][1,4]dioxin-6-yl)-N-isobutylthiazole-5-carboxamide The title compound (yield: 65.87%) was obtained as a white solid in the same manner as in Example 3, except that 2-chloro-N-isopropylthiazole-5-carboxamide was used instead of 5-chloro-N-isopropylthiophene-2-carboxamide.

$^{1}$H NMR (400 MHz, DMSO-d6) δ 8.63 (t, 1H, J=5.8 Hz), 8.36 (s, 1H), 7.45-7.38 (m, 2H), 6.95 (d, 1H, J=8.6 Hz), 4.28 (s, 4H), 3.05 (t, 2H, J=6.4 Hz), 1.86-1.73 (m, 1H), 0.87 (d, 6H, J=6.7 Hz); $^{13}$C NMR (100 MHz, DMSO-d6) δ 169.9, 160.1, 146.3, 144.1, 143.9, 135.3, 126.5, 120.3, 118.3, 115.2, 64.8, 64.5, 47.0, 28.6, 20.6, 20.6; ESI (m/z) 319 (MH$^{+}$)

Example 17: Preparation of 2-(benzo[d][1,3]dioxol-5-yl)-N-phenylthiazole-5-carboxamide The title compound (yield: 75.82%) was obtained as a yellow solid in the same manner as in Example 2, except that 2-chloro-N-phenylthiazole-5-carboxamide was used instead of 5-chloro-N-isopropylthiophene-2-carboxamide.

$^1$H NMR (400 MHz, DMSO-d6) δ 10.39 (s, 1H), 8.59 (s, 1H), 7.70 (d, 2H, J=7.8 Hz), 7.55 (dd, 1H, $J_A$=8.1, $J_B$=1.7 Hz), 7.52 (d, 1H, J=1.5 Hz), 7.35 (t, 2H, J=7.9 Hz), 7.11 (t, 1H, J=7.4 Hz), 7.03 (d, 1H, J=8.1 Hz), 6.12 (s, 2H); $^{13}$C NMR (100 MHz, DMSO-d6) δ 170.9, 158.9, 150.2, 148.6, 144.9, 138.8, 135.2, 129.1, 129.1, 127.2, 124.4, 122.0, 120.8, 120.8, 109.3, 106.6, 102.3; ESI (m/z) 325 (MH$^+$)

Example 18: Preparation of 2-(2,3-dihydrobenzo[b][1,4]dioxin-6-yl)-N-phenylthiazole-5-carboxamide The title compound (yield: 45.13%) was obtained as a yellow solid in the same manner as in Example 3, except that 2-chloro-N-phenylthiazole-5-carboxamide was used instead of 5-chloro-N-isopropylthiophene-2-carboxamide.

$^1$H NMR (400 MHz, DMSO-d6) δ 10.39 (s, 1H), 8.59 (s, 1H), 7.70 (d, 2H, J=7.9 Hz), 7.51-7.45 (m, 2H), 7.35 (t, 2H, J=7.8 Hz), 7.11 (t, 1H, J=7.3 Hz), 6.98 (d, 1H, J=8.1 Hz), 4.29 (s, 4H); $^{13}$C NMR (100 MHz, DMSO-d6) δ 170.8, 158.9, 146.5, 145.0, 144.2, 138.8, 135.2, 129.1, 129.1, 126.4, 124.4, 120.8, 120.8, 120.4, 118.3, 115.3, 64.8, 64.5; ESI (m/z) 339 (MH$^+$), 337 (MH$^-$)

Example 19: Preparation of methyl 5-(benzo[d][1,3]dioxol-5-yl)thiophene-2-carboxylate Methyl 5-chlorothiophene-2-carboxylate (176 mg, 0.996 mmol), benzo[d][1,3]dioxol-5-ylboronic acid (248.03 mg, 1.495 mmol), sodium carbonate (633.70 mg, 5.979 mmol) and palladium (II) acetate (34.97 mg, 0.05 mmol) were added to 1,2-dimethoxyethane (4 mL) and double distilled water (1 mL), and the mixture was stirred at 120° C. for 200 minutes together with ultrasonic treatment and then extracted three times with dichloromethane. The extracted solution was dried over anhydrous magnesium sulfate. The organic solvent was concentrated under reduced pressure, purified by flash column chromatography (n-Hx: EtOAc=3:1) and then dried by a vacuum pump to give the title compound as a white solid (yield: 27.47%).

$^1$H NMR (400 MHz, DMSO-d6) δ 7.74 (d, 1H, J=5.2 Hz), 7.48 (d, 1H, J=3.2 Hz), 7.35 (s, 1H), 7.23 (d, 1H, J=8.0 Hz), 6.97 (d, 1H, J=8.0 Hz), 6.07 (s, 2H), 3.81 (s, 3H)

Example 20: Preparation of ethyl 2-(benzo[d][1,3]dioxol-5-yl)thiazole-5-carboxylate Ethyl 2-bromothiazole-5-carboxylate (200 mg, 0.847 mmol), benzo[d][1,3]dioxol-5-ylboronic acid (210.86 mg, 1.271 mmol), sodium carbonate (538.73 mg, 5.083 mmol) and palladium (II) acetate (27.73 mg, 0.042 mmol) were added to 1,2-dimethoxyethane (4 mL) and double distilled water (1 mL), and the mixture was stirred at 120° C. for 200 minutes together with ultrasonic treatment and then extracted three times with dichloromethane. The extracted solution was over anhydrous magnesium sulfate. The organic solvent was concentrated under reduced pressure, purified by flash column chromatography (n-Hx: EtOAc=3:1) and then dried by a vacuum pump to give the title compound as a white solid (yield: 8.56%).

$^1$H NMR (400 MHz, DMSO-d6) δ 8.40 (s, 1H), 7.57 (dd, 1H, $J_A$=8.1 Hz, $J_B$=1.5 Hz), 7.52 (d, 1H, J=1.4 Hz), 7.04 (d, 1H, J=8.1 Hz), 6.12 (s, 2H), 4.31 (q, 2H, J=7.1 Hz), 1.29 (t, 3H, J=7.1 Hz); ESI (m/z) 278 (MH$^+$)

Experimental Example 1: Effect of Activation of Autophagy

1) Method for Autophagy Activation

Primary hepatocyte was isolated from male C57BL/6 mice by a collagenase perfusion method which is a known method (Gastroenterology 2011, 141, 2188). Survival rate of the isolated cells was measured by trypan blue exclusion method. Autophagy was induced by ischemia-reperfusion method (Gastroenterology 2011, 141, 2188).

Specifically, in order to induce ischemia, hepatocytes were incubated at 37° C. in Krebs-Ringer-HEPES (KRH0) buffer (pH 6.2) in an anaerobic chamber for 2 hours. The respective hepatocytes were treated with DMSO, the compound prepared in Examples described above, or Rapamycin as a control substance, and then KRH buffer solution at pH 7.4 was treated under aerobic conditions for 1 hour to induce reperfusion. Subsequently, hepatocytes were lysed with an extraction buffer containing protease inhibitor cocktail (PBS solution containing 0.5% Triton X-100, 1 mM Na3VO4, etc.), and then fragmentation of DNA was performed by sonication. The amount of protein was measured with bovine serum albumin as a protein standard using Bio-Rad Protein Assay Kit (Cat No. 500-0002). After electrophoresis of 10-50 μg of total cell protein in 8-12% (w/v) polyacrylamide gel containing 0.1% SDS, and then the proteins present in a gel were transferred to PVDF membrane by electroblotting. Then, in order to block non-specific binding, the PVDF membrane was placed in a TBS-tween (tris-buffered saline-tween, Sigma Co.) solution containing 5% nonfat dry milk and reacted at room temperature for 1 hour. The filter was placed in a TBS-tween solution containing an antibody against LC3 protein (Cell Signaling), allowed to stand at 4° C. for 12 hours, and then labeled with a secondary antibody labeled with HRP (Horseradish Peroxidase, Sigma Co., Cat No. P0889). Then, bands were measured using ECL (Enhanced Chemiluminescence, Thermo Scientific, Cat No. 34080).

2) Results of Measurement of Autophagy Activation

The induction of autophagy can be confirmed by an increase in specific LC3-II molecules. LC3 precursors are usually scattered in the cytoplasm, subjected to proteolytic cleavage, and present in the form of LC3-I. When autophagy is activated, the C-terminal glycine is modified to form LC3-II, which migrates to autophagosome and is distributed in puncta form.

The measurement results are shown in Table 1 below. The amount of LC3-II increased by the compound treatment was quantified by measuring the band density, and then compared with the amount of LC3-II increased by the treatment of Rapamycin used as a control substance, and the comparison values are shown in Table 1. That is, the case having the same autophagy-inducing capacity as that of Rapamycin used as a control substance is represented by a value of 1; the case having superior autophagy-inducing capacity to that of Rapamycin is represented by a value greater than 1; and the case having weaker autophagy-inducing capacity than that of Rapamycin is represented by a value less than 1.

TABLE 1

| Example No. | Autophagy-inducing capacity |
| --- | --- |
| 1 | 2.02 |
| 2 | 1.92 |
| 3 | 0.88 |
| 4 | 1.33 |
| 5 | 2.05 |
| 6 | 1.11 |
| 7 | 1.52 |
| 8 | 1.24 |
| 9 | 1.39 |
| 10 | 0.65 |
| 11 | 0.88 |
| 12 | 0.54 |
| 13 | 0.73 |
| 14 | 0.57 |
| 15 | 0.29 |
| 16 | 0.78 |
| 17 | 1.39 |
| 18 | 1.27 |
| 19 | 0.77 |
| 20 | 0.79 |
| Rapamycin | 1 |

As shown in Table 1 above, it can be confirmed by an increase in LC3-II that hepatocytes induce autophagy by the treatment of Rapamycin used as a control substance in ischemia-reperfusion model. Also, the compound according to the present invention showed an increase in LC3-II by more than twice as compared with Rapamycin used as a control substance. Therefore, it can be seen that the compounds according to the present invention had superior autophagy-inducing capacity to rapamycin.

Figure 1:
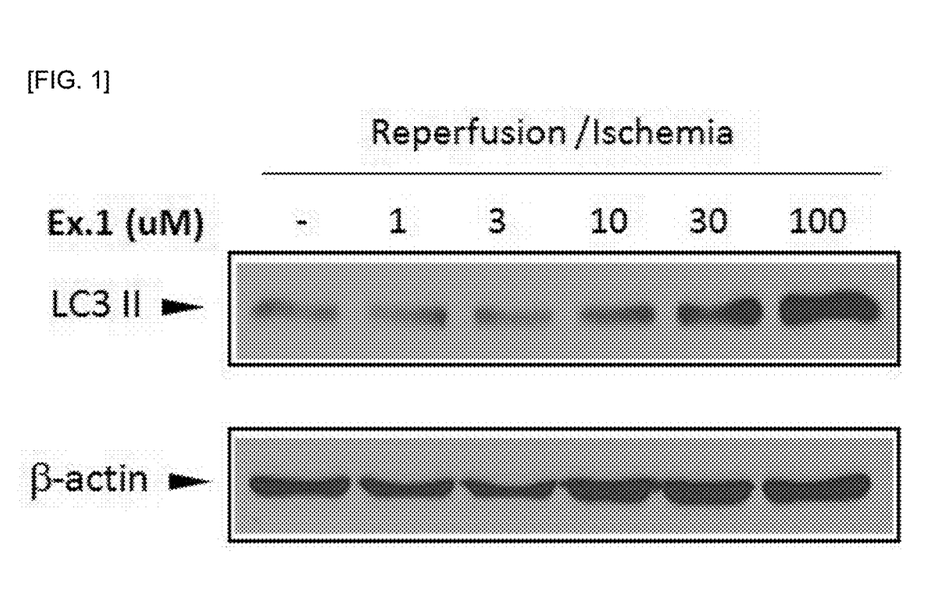
FIG. 1 and FIG. 2 show the results of confirming by an increase in LC3-II that autophagy is significantly increased by the treatment of the compound prepared in one example of the present invention in ischemia-reperfusion model using primary hepatocytes.
Figure 2:
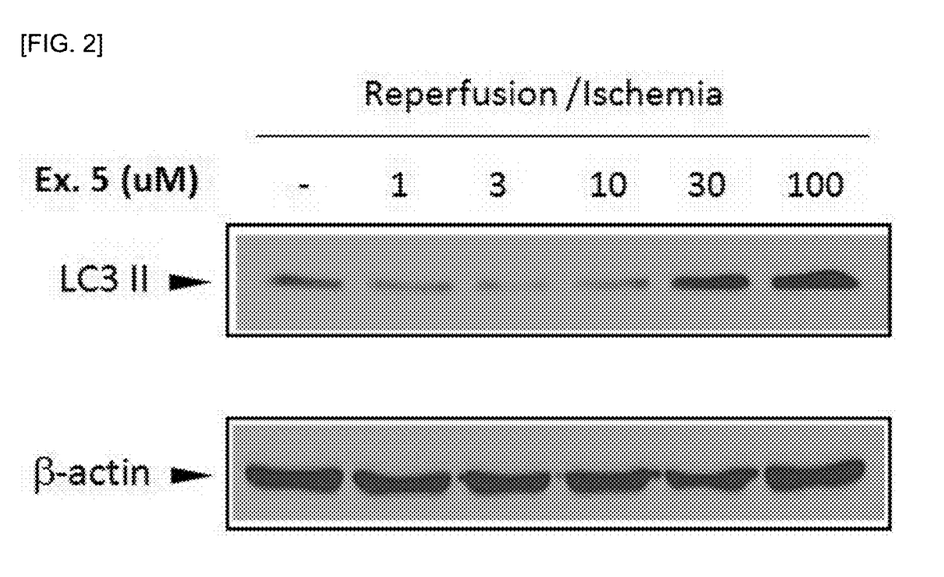

In addition, FIG. 1 and FIG. 2 show the results of Western immunoblotting of some compounds having excellent autophagy-inducing capacity. As shown in FIG. 1 and FIG. 2, it can be confirmed by an increase in LC3-II that hepatocytes exhibited a significant increase in autophagy induction by treatment of the compounds of Examples 1 and 5 in ischemia-reperfusion model.

Experimental Example 2: Effect of Inhibition of mTOR Enzyme Activity

1) Method of Measurement of mTOR Enzyme Activity

Western immunoblotting was performed using the cell-disrupted liquid obtained in Experimental Example 1. The PVDF membrane obtained from electrophoresis and electroblotting was placed in a TBS-tween solution containing an antibody against mTOR or p-mTOR (Ser 2448) proteins (Cell Signaling), allowed to stand at 4° C. for 12 hours, and then labeled with a secondary antibody labeled with HRP (Horseradish Peroxidase, Sigma Co., Cat No. P0889). Then, bands were measured using ECL (Enhanced Chemiluminescence, Thermo Scientific, Cat No. 34080).

2) Results of Measurement of mTOR Enzyme Activity

Figure 3:
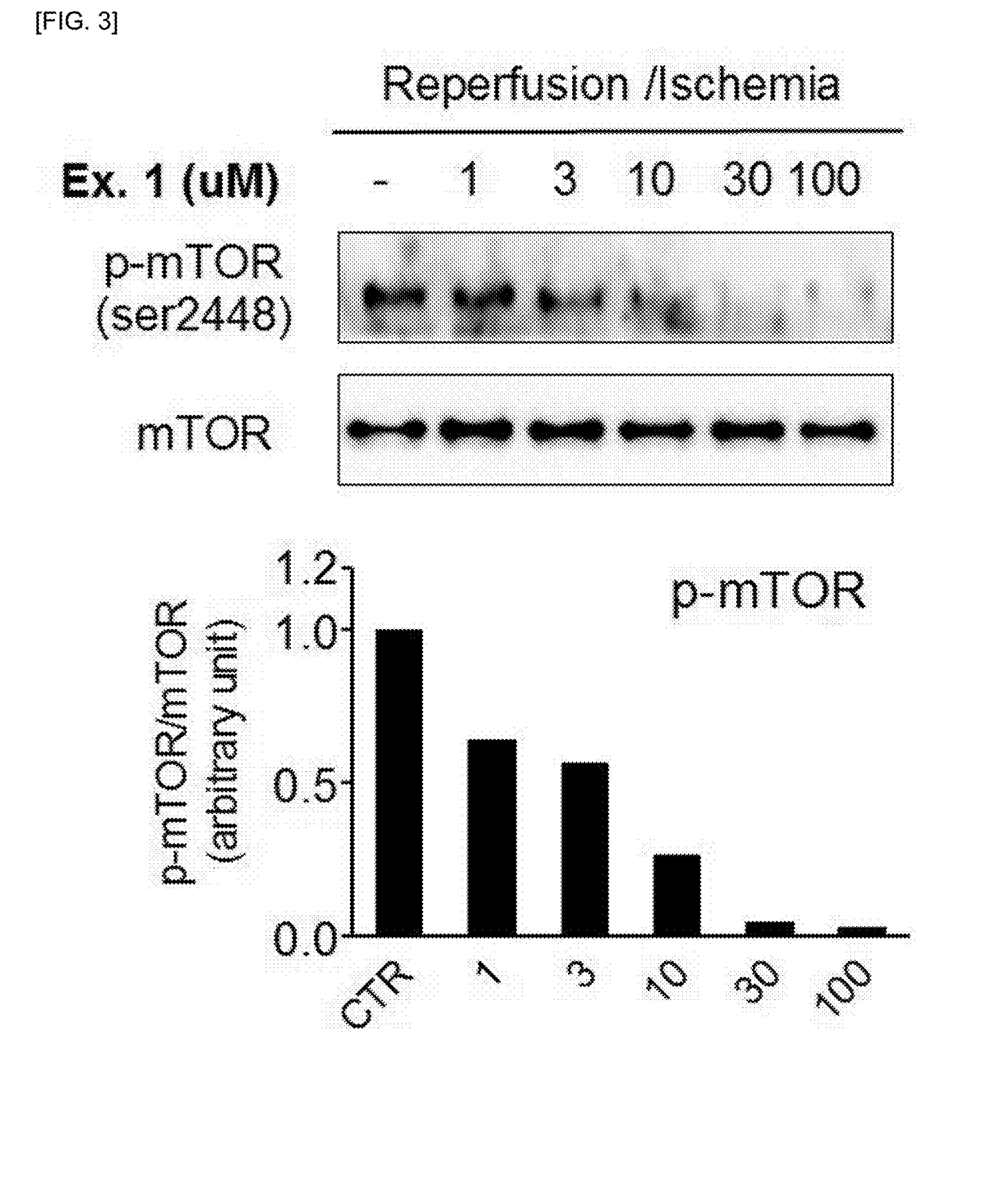
FIG. 3 shows that hepatocyte inhibits mTOR activation by the treatment of the compound prepared in one example of the present invention in ischemia-reperfusion model, which shows the results confirming that the phosphorylation of mTOR at 2448 position is significantly inhibited.

The measurement results are shown in FIG. 3. mTOR is known to be one of the major proteins regulating autophagy. mTOR serves to inhibit autophagy at a quiescent state, whereas phosphorylation at serine 2448-position inhibits the function of mTOR, resulting in activation of autophagy. As shown in FIG. 3, it was confirmed that hepatocytes significantly inhibited the phosphorylation of mTOR at serine 2448 position by the treatment of the compound of Example 1 in ischemia-reperfusion model Experimental Example 3: Effect in a Model of Induced Acute Liver Injury Attempts were made to confirm the inhibitory effect of autophagy activator on liver injury in an animal model of induced liver fibrosis due to acute liver injury. In order to confirm the effect of inhibiting acute liver injury, carbon tetrachloride ($CCl_4$) was administered to C57BL/6 mice to induce acute liver injury, and then the compound according to the present invention was administered. It was then confirmed whether liver injuries were inhibited.

1) Experimental Method

Five-week-old female C57BL/6 mice were introduced and acclimated for one week, and then divided into six groups respectively; a normal control group, a group to which carbon tetrachloride was administered, and groups to which the compounds according to the present invention (Examples 1, 2, 5, and 7) were administered. Each of the compounds according to the present invention was dissolved in corn oil and administered orally three times at a dose of 50 mg/kg (body weight) every 12 hours. 30 Minutes after final oral administration, carbon tetrachloride was intraperitoneally administered at a dose of 5 mL/kg (body weight) and then autopsied 24 hours later top remove a sample of liver tissue under autopsy and fix it, thereby preparing a tissue specimen. After preparation of tissue specimen slides, H & E staining was performed and liver injuries were confirmed with a microscope.

2) Experimental Result

Figure 4:
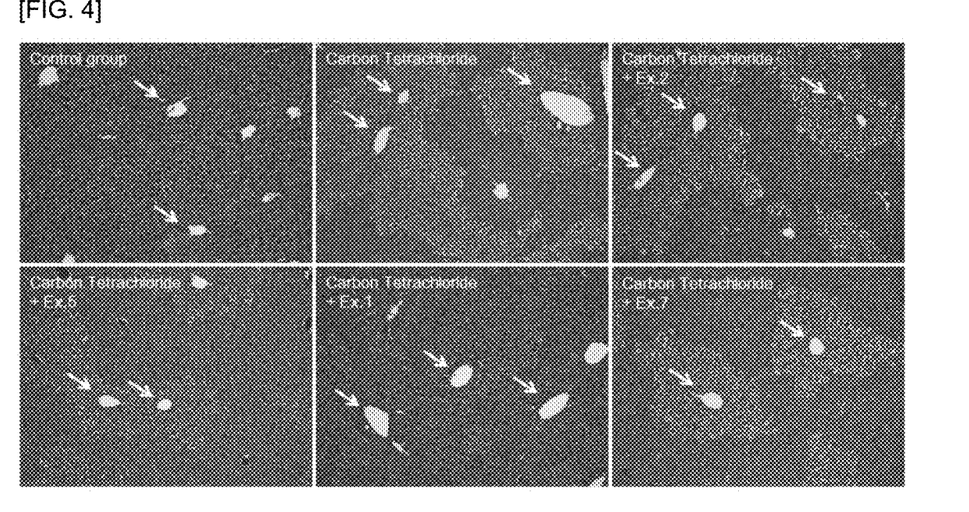
FIG. 4 shows the results of histologically confirming the acute liver injury induced by carbon tetrachloride and the therapeutic effect of the compound prepared in one example of the present invention through H & E staining. The arrows in FIG. 4 represents a portal vein.
Figure 5:
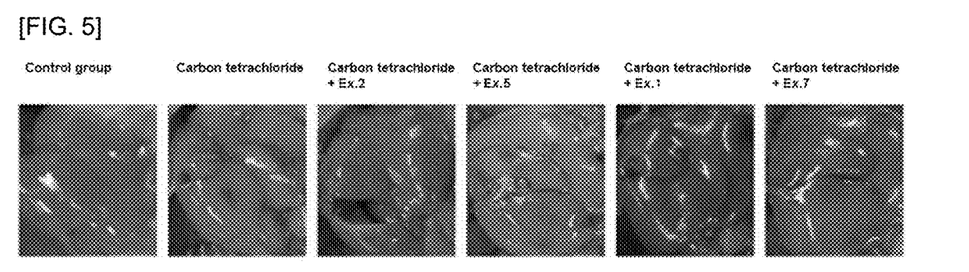
FIG. 5 shows the results of observing morphological abnormalities of liver during autopsy after induction of acute liver injury.

It can be observed that acute liver injury induced by carbon tetrachloride is characterized by necrosis of hepatocytes at the adjacent site of the portal vein and that fat granules are accumulated in damaged liver cells. After administration of carbon tetrachloride and four compounds according to the present invention in experimental animals, liver tissue specimens were prepared by autopsy. Liver injury as well as inhibitory effect of autophagy activator on liver injury were confirmed through H & E staining (FIG. 4). As shown in FIG. 4, in the group to which carbon tetrachloride alone was administered, necrosis of hepatocytes located in the vicinity of the portal vein was confirmed, and fat granules of injured hepatocytes were observed, indicating that acute liver injury was induced by carbon tetrachloride. In the groups to which Examples 1 and 5 according to the present invention were administered, it was observed that the liver injury was clearly recovered. In the groups to which Examples 2 and 7 were administered, the recovery effect of liver injury was relatively small. In addition, the presence or absence of liver injury during autopsy was confirmed with naked eyes, and no morphological abnormalities were observed in the liver of all the groups (FIG. 5).

Experimental Example 4: Effect in a Model of Induced Liver Fibrosis

In order to confirm the effect of inhibiting liver fibrosis caused by chronic liver injury, thioacetamide (TAA) was administered to C57BL/6 mice to induce chronic liver injury, thereby inducing liver fibrosis, and then the compounds according to the present invention were administered. It was then confirmed whether chronic liver injuries were inhibited.

1) Experimental Method

Five-week-old female C57BL/6 mice were introduced and acclimated for one week, and then divided into six groups respectively; a normal control group, a group to which thioacetamide was administered, and groups to which the compounds according to the present invention (Examples 2, 5 and 7) were administered. Thioacetamide was dissolved in phosphate-buffered physiological saline and administered intraperitoneally at a dose of 200 mg/kg (body weight) three times a week, for a total of 6 weeks. Three compounds according to the present invention was dissolved in corn oil at a final 6 weeks and administered orally at a dose of 50 mg/kg (body weight) once a day for a total of 8 days. Twenty-four hours after the final oral administration, an autopsy was performed to remove a sample of liver tissue and fix it, thus preparing a tissue specimen. After preparation of tissue specimen slides. H & E staining was performed, and liver tissue injury as well as inflammatory cell infiltration in liver tissue were confirmed by microscopy. In addition, Masson's Trichrome staining was performed, and collagen deposition in the liver tissue was confirmed by a microscope.

2) Experimental Result

Histologically, liver fibrosis deposits collagen in the capillary network of liver tissue, which is deposited in the form of lobules surrounding the central vein of the liver. This can be observed using Masson's Trichrome staining. After the administration of thioacetamide and the compounds according to the present invention, the presence or absence of liver injuries during autopsy was confirmed with naked eyes.

Figure 6:
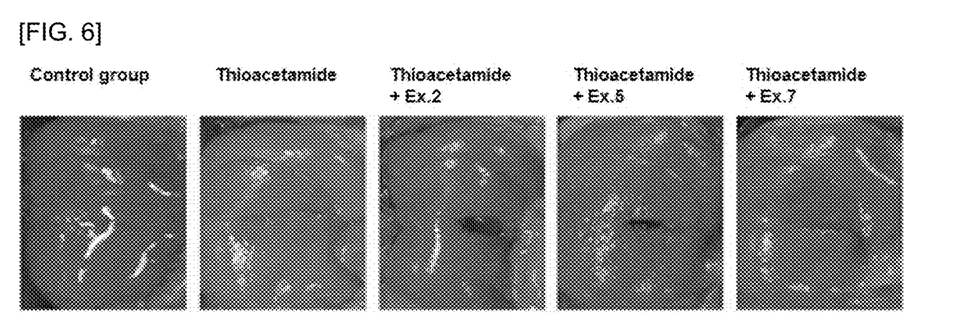
FIG. 6 shows the results of observing morphological abnormalities of liver during autopsy after administration of thioacetamide for inducing liver fibrosis and the compound prepared in one example of the present invention.
Figure 7:
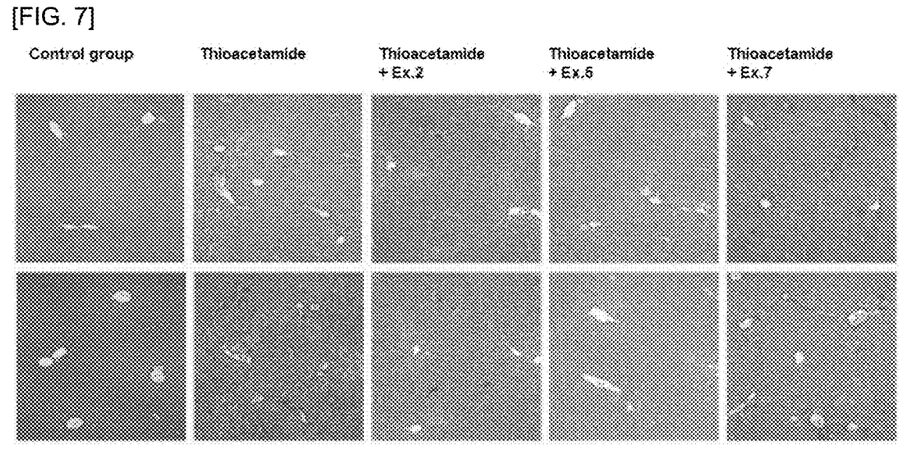
FIG. 7 shows the results of confirming, through Masson's Trichrome staining, the collagen deposition of liver tissue sections removed after administration of thioacetamide and the compound prepared in one example of the present invention.
Figure 8:
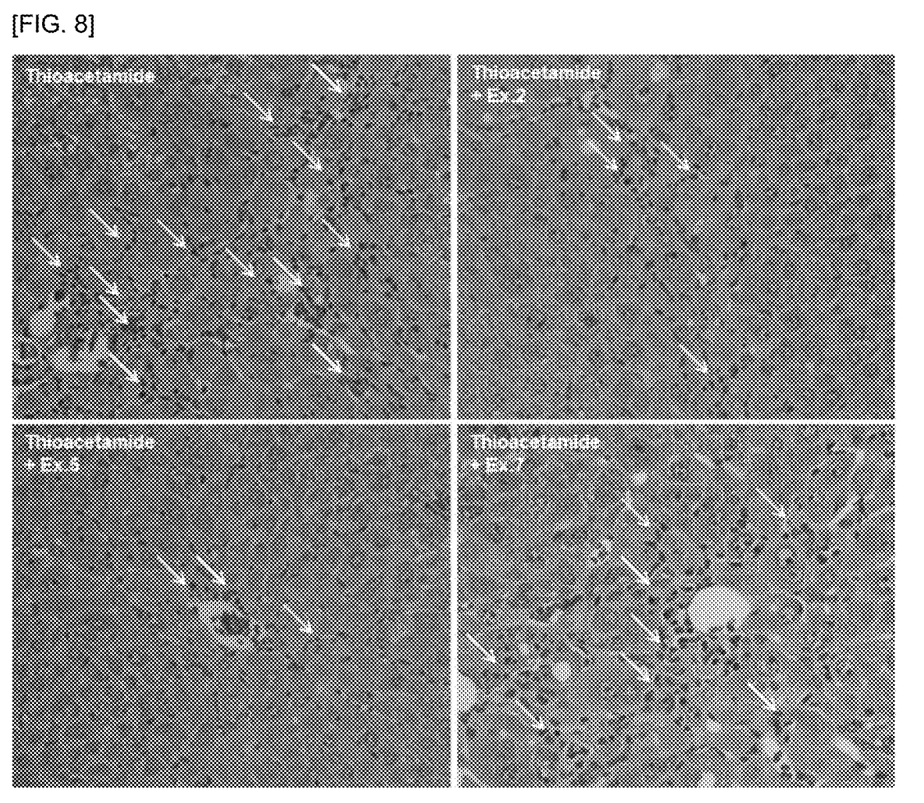
FIG. 8 shows the results of histologically confirming infiltration of inflammatory cells in liver tissue damaged due to thioacetamide through H & E staining.

Morphologically, in the liver of the control group, the surface was smooth and no abnormalities were observed, whereas in all groups in which liver injuries were induced by thioacetamide, fine nodules were observed on the surface of the liver and the liver sizes were all similar (FIG. 6). It was confirmed by microscopic observation with Masson's Trichrome staining that liver fibrosis was induced by the administration of thioacetamide for 6 weeks. It was also confirmed that fibrosis was alleviated by the administration of the compounds according to the present invention (FIG. 7). In particular, it was observed that fibrosis was clearly alleviated by Examples 2 and 5 according to the present invention (FIG. 7). In addition, it was observed that the infiltration of inflammatory cells, which play an important role in fibrosis, was reduced by treating the compounds according to the present invention (FIG. 8).

Experimental Example 5: Effect in a Model of Induced Liver Fibrosis

In order to confirm the effect of inhibiting liver fibrosis caused by chronic liver injury, carbon tetrachloride was administered to C57BL/6 mice to induce chronic liver injury, thereby inducing liver fibrosis, and then the compounds according to the present invention were administered. It was then confirmed whether chronic liver injuries were inhibited.

1) Experimental Method

Five-week-old female C57BL/6 mice were introduced and acclimated for one week, and then divided into six groups respectively; a normal control group, a group to which carbon tetrachloride was administered, and groups to which the compounds according to the present invention (Examples 1 and 5) were administered. Carbon tetrachloride was dissolved in corn oil and administered intraperitoneally at a dose of 0.8 ml/kg (body weight) twice a day, for a total of 8 days. Twenty-four hours after the final oral administration, an autopsy was performed to remove a sample of liver tissue and fix it, thus preparing a tissue specimen. After preparation of tissue specimen slides, H & E staining was performed, and liver tissue injury as well as inflammatory cell infiltration in liver tissue were confirmed by microscopy. In addition, Masson's Trichrome staining was performed, and collagen deposition in the liver tissue was confirmed by microscope.

2) Experimental Result

Figure 9:
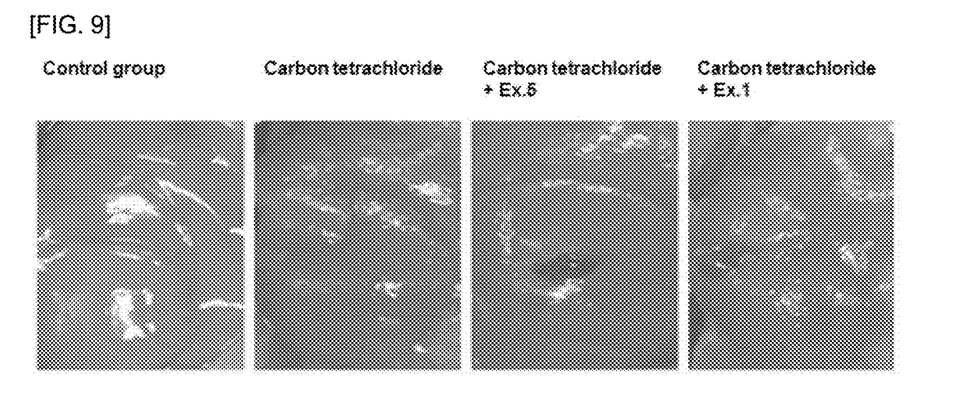
FIG. 9 shows the results of observing morphological abnormalities of liver during autopsy after administration of carbon tetrachloride for inducing liver fibrosis and the compound prepared in one example of the present invention.
Figure 10:
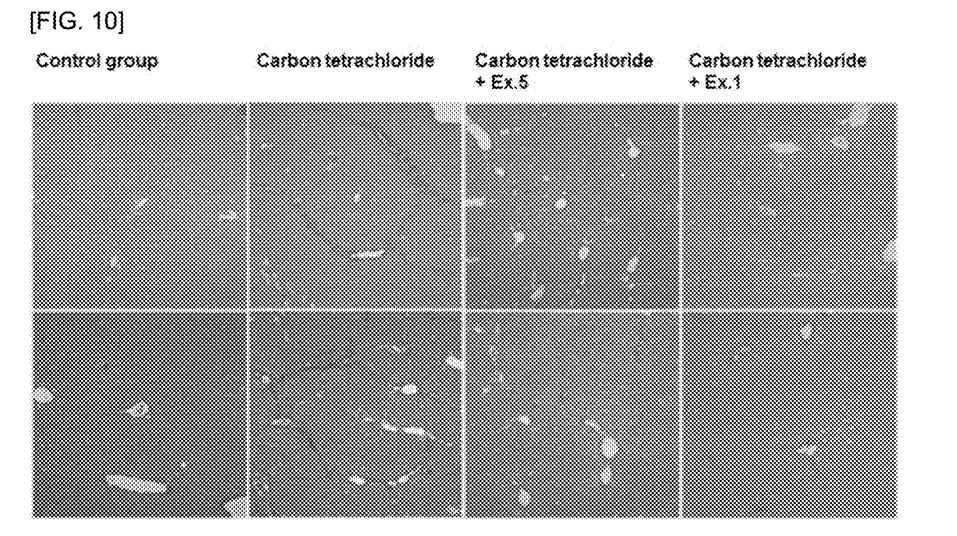
FIG. 10 shows the results of confirming, through Masson's Trichrome staining, the collagen deposition in liver tissue sections removed after administration of carbon tetrachloride and the compound prepared in one example of the present invention.

After the administration of carbon tetrachloride and autophagy activator, the presence or absence of liver injuries during autopsy was confirmed with naked eyes. Morphologically, in the liver of the control group, the surface was smooth and no abnormalities were observed, whereas in all groups in which liver injuries were induced by carbon tetrachloride, fine nodules were observed on the surface of the liver, and the liver sizes were all similar (FIG. 9). It was confirmed by Masson's Trichrome staining in liver tissue slide sections that liver fibrosis was induced by the administration of carbon tetrachloride for 8 weeks. It was also confirmed that fibrosis was alleviated by the administration of the compounds (Examples 1 and 5) according to the present invention (FIG. 10). In addition, it was confirmed that the effect of Example 1 was relatively greater in light of the fact that collagen deposition was less in the group treated with Example 1 than in the group treated with Example 5.

Experimental Example 6: Effect in a Model of Induced Liver Fibrosis

In order to confirm the effect of inhibiting liver fibrosis caused by chronic liver injury, bile duct ligation (BDL) was performed in Sprague Dawley (SD) rats to induce chronic liver injury, thereby inducing liver fibrosis, and then the compounds according to the present invention were administered. It was then confirmed whether chronic liver injuries were inhibited.

1) Experimental Method

Seven-week-old female SD rats were introduced and acclimated for one week, and then divided into five groups respectively; a control group, a bile duct ligation surgery group, and groups to which the compound according to the present invention (Example 15) was administered at three doses (12.5, 25 and 50 mg/kg body weight). In the control group, the bile duct was not exposed or ligated after laparotomy, and the other groups performed bile duct ligation surgery. One week after bile duct ligation, the compound according to the present invention (Example 1) was dissolved in corn oil and administered orally for each dose once a day for a total of 14 days. Twenty-four hours after the final administration, an autopsy was performed to remove a sample of liver tissue and fix it, thus preparing a tissue specimen. After preparation of tissue specimen slides. H & E staining was performed, and collagen deposition in liver tissue were confirmed by microscopy. In addition, a part of the removed liver (10 mg) was decomposed to perform a quantitative experiment of hydroxyproline which is a major component of collagen, and the amount of collagen deposited was quantified, thereby confirming the effects of the compound according to the present invention.

2) Experimental Result

Figure 11:
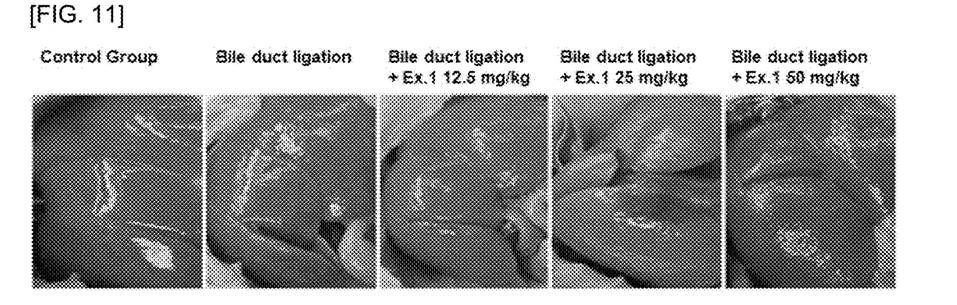
FIG. 11 shows the results of observing morphological abnormalities of liver during autopsy after bile duct ligation surgery is performed to induce liver fibrosis.
Figure 12:
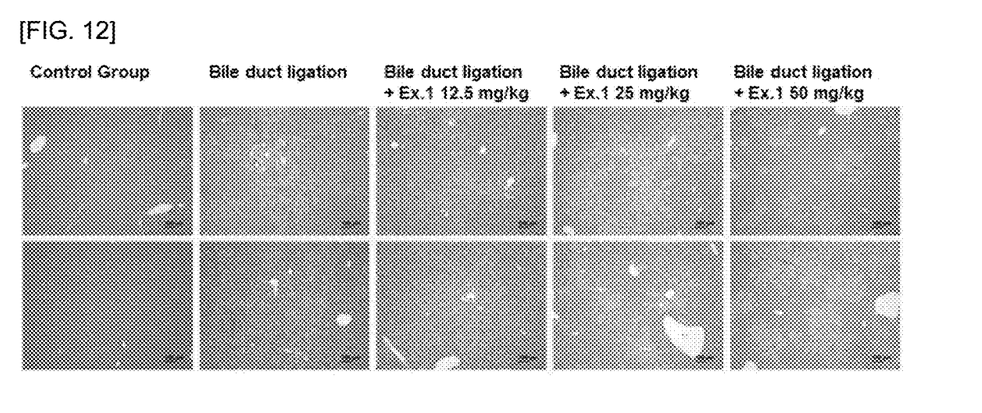
FIG. 12 shows the results of confirming, through Masson's Trichrome staining, the collagen deposition in liver tissue sections removed after bile duct ligation surgery.

After the bile duct ligation surgery and the administration of the compounds according to the present invention, the presence or absence of liver injuries during autopsy was confirmed with naked eyes. Morphologically, in the liver of the control group, the surface was smooth and no abnormalities were observed, whereas in all groups in which liver injuries were induced by bile duct ligation, fine nodules were observed on the surface of the liver and the liver sizes were larger than that of the control group (FIG. 11). There was no significant difference between the group treated only with the bile duct ligation and the groups treated with the bile duct ligation surgery and the compounds according to the present invention (FIG. 11). It was confirmed by Masson's Trichrome staining in liver tissue slide sections that liver injury and fibrosis were induced by bile duct ligation. It was confirmed that liver fibrosis progressed in the vicinity of the central vein was alleviated by the administration of the compounds according to the present invention (FIG. 12).

Figure 13:
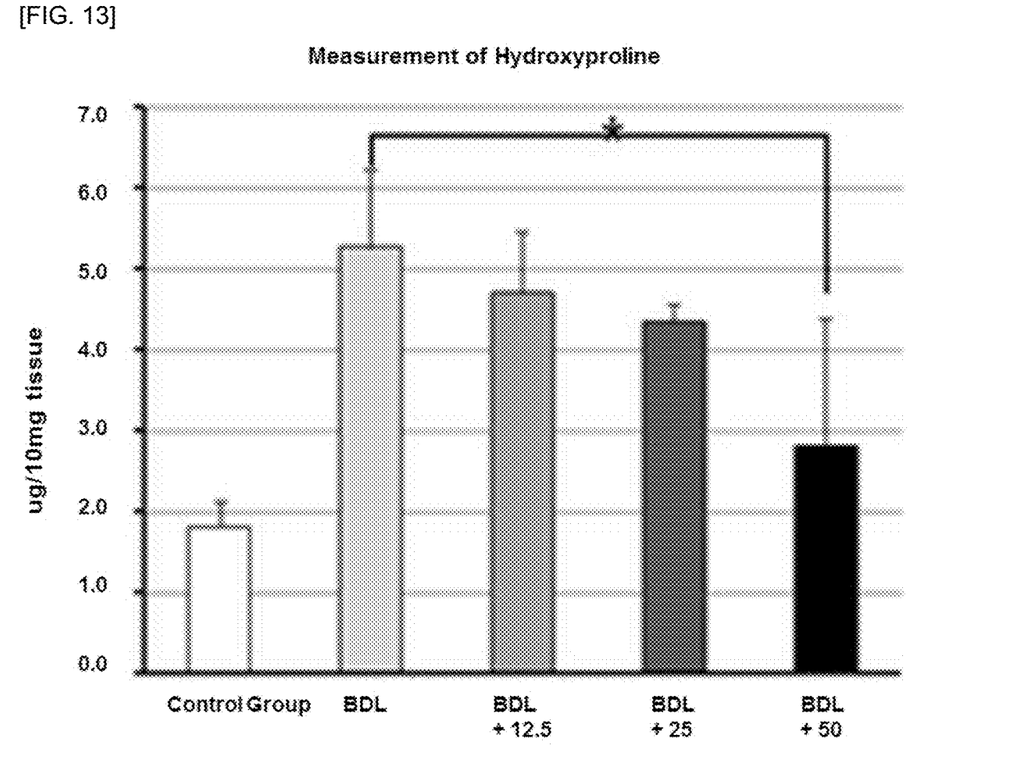
FIG. 13 shows the results of quantitative experiment of hydroxyproline using liver tissue removed after bile duct ligation surgery.

Similarly, a quantitative experiment of hydroxyproline for quantitatively determining the amount of collagen deposited in the liver tissue was carried out. As a result, it was found that the larger the quantity of the compound according to the present invention (Example 1), the smaller the collagen deposition (FIG. 13). In addition, in all groups treated with the compounds according to the present invention, the number of injured hepatocytes adjacent to the portal vein was markedly reduced as compared to the untreated group, confirming that liver injuries were alleviated histologically (FIG. 11).

The invention claimed is:

1. A compound represented by Chemical Formula 1 below, or a pharmaceutically acceptable salt thereof:

[Chemical Formula 1]

wherein, in Chemical Formula 1, $R_1$ and $R_2$ are each independently $C_{1-4}$ alkyl, $R_3$ is $C_{1-4}$ alkyl, $C_{1-4}$ alkyl substituted with $C_{5-10}$ heteroaryl, $C_{6-10}$ aryl, X is CH, and

Y is NH.

2. The compound or a pharmaceutically acceptable salt thereof according to claim 1, wherein $R_1$ and $R_2$ are methyl.

3. The compound or a pharmaceutically acceptable salt thereof according to claim 1, wherein $R_3$ is methyl, ethyl, isopropyl, isobutyl, pyridinylmethyl, or phenyl.

4. The compound represented by Chemical Formula 4 below, or a pharmaceutically acceptable salt thereof:

[Chemical Formula 4]

wherein, in Chemical Formula 4:

$R_1$ and $R_2$ are connected together to form $C_{1-4}$ alkylene, $R_3$ is phenyl, X is N, and Y is NH.

5. The compound or a pharmaceutically acceptable salt thereof according to claim 1, wherein $R_1$ and $R_2$ are methyl, $R_3$ is isopropyl, isobutyl, or phenyl, X is CH, and Y is NH.

6. The compound or a pharmaceutically acceptable salt thereof, wherein the compound is any one selected from the group consisting of:

5-(3,4-dimethoxyphenyl)-N-isopropylthiophene-2-carboxamide, 5-(3,4-dimethoxyphenyl)-N-isopropylthiophene-2-carboxamide,

5-(3,4-dimethoxyphenyl)-N-phenylthiophene-2-carboxamide, 2-(benzo[d][1,3]dioxol-5yl)-N-phenylthiazole-5-carboxamide, and

2-(2,3-dihydrobenzo[b][1,4]dioxin-6-yl)-N-isopropylthiophene-5-carboxamide.

7. A method for preparing a compound represented by Chemical Formula 1 below, comprising reacting a compound represented by Chemical Formula 2 below and a compound represented by Chemical Formula 3 below to prepare a compound represented by Chemical Formula 1 blow:

[Chemical Formula 1]

[Chemical Formula 2]

[Chemical Formula 3]

in Chemical Formulae 1 to 3,
$R_1$, $R_2$, $R_3$, X and Y are as defined in claim 1, and
$R_4$ is halogen.

8. A pharmaceutical composition for treating liver diseases, comprising the compound of claim 1 or a pharmaceutically acceptable salt thereof.

9. The pharmaceutical composition according to claim 8, wherein the liver diseases are liver fibrosis, liver cirrhosis, hepatitis, alcoholic liver disease, fatty liver, or non-alcoholic steatohepatitis.

10. A pharmaceutical composition for treating liver diseases, comprising the compound of claim 4 or a pharmaceutically acceptable salt thereof.

11. The pharmaceutical composition according to claim 10, wherein the liver diseases are liver fibrosis, liver cirrhosis, hepatitis, alcoholic liver disease, fatty liver, or non-alcoholic steatohepatitis.

12. A pharmaceutical composition for treating liver diseases, comprising the compound of claim 6 or a pharmaceutically acceptable salt thereof.

13. The pharmaceutical composition according to claim 12, wherein the liver diseases are liver fibrosis, liver cirrhosis, hepatitis, alcoholic liver disease, fatty liver, or non-alcoholic steatohepatitis.

\* \* \* \* \*